United States Patent [19]

Huber

[11] Patent Number: 4,616,639

[45] Date of Patent: Oct. 14, 1986

[54] ORTHOPEDIC BELT WITH LEG SUPPORTS

[76] Inventor: William C. Huber, 3751 E. Fairway Dr., Birmingham, Ala. 35213

[21] Appl. No.: 570,072

[22] Filed: Jan. 10, 1984

[51] Int. Cl.$^4$ ............................................. A61F 13/00
[52] U.S. Cl. ....................................... 128/99; 128/165; 128/400
[58] Field of Search ................. 128/78, 95, 96, 99, 128/100, 106, 399, 402, 133, 134; 5/443, 444

[56] References Cited

U.S. PATENT DOCUMENTS

| | | | |
|---|---|---|---|
| 1,940,904 | 12/1933 | Dayton et al. | 128/78 |
| 2,573,791 | 11/1951 | Howells | 128/402 |
| 3,154,072 | 10/1964 | Mack | 128/78 |
| 3,901,228 | 8/1975 | Branen | 128/80 R |
| 3,955,565 | 5/1976 | Johnson, Jr. | 128/89 R |
| 4,081,150 | 3/1978 | Tyson | 128/402 |
| 4,135,504 | 1/1979 | Spann | 5/444 |
| 4,178,923 | 12/1979 | Curlee | 128/78 |
| 4,364,135 | 12/1982 | Giesche | 5/443 |
| 4,470,417 | 9/1984 | Gruber | 128/402 |

Primary Examiner—C. Fred Rosenbaum
Assistant Examiner—Karen Kaechele
Attorney, Agent, or Firm—Harvey B. Jacobson

[57] ABSTRACT

Apparatus for decreasing stresses and pressure generated to a person's lumbosacral spine while sitting or lying supine, prone, or on the side comprises a belt which fits around the waist, and leg supports which attach to the wearer's legs between the knee and ankle. The belt has a series of foam pads positioned in such a way to help maintain the correct anatomical position of the lumbosacral spine while the person is sitting or lying down, and the leg supports are designed to minimize forces generated in the lumbosacral area from muscular tension. Such stresses and pressures may include; stretching forces on the outer wall of the disc, the annulus fibrosis, stretching forces on the ligaments, stretching forces on the back muscles, and intradiscal pressure.

12 Claims, 9 Drawing Figures

U.S. Patent    Oct. 14, 1986    Sheet 1 of 2    4,616,639
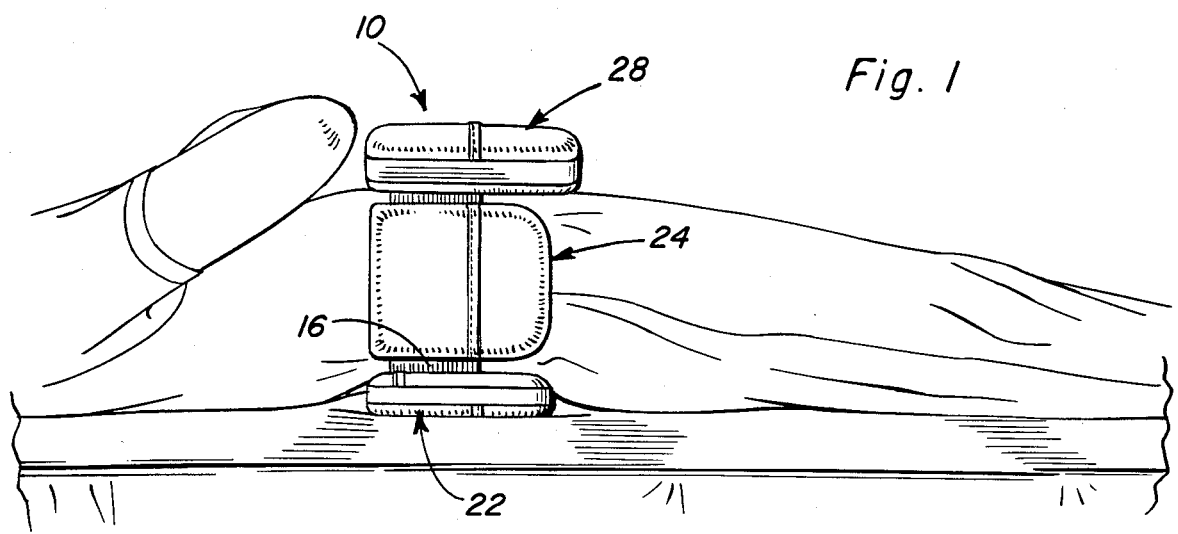
Fig. 1
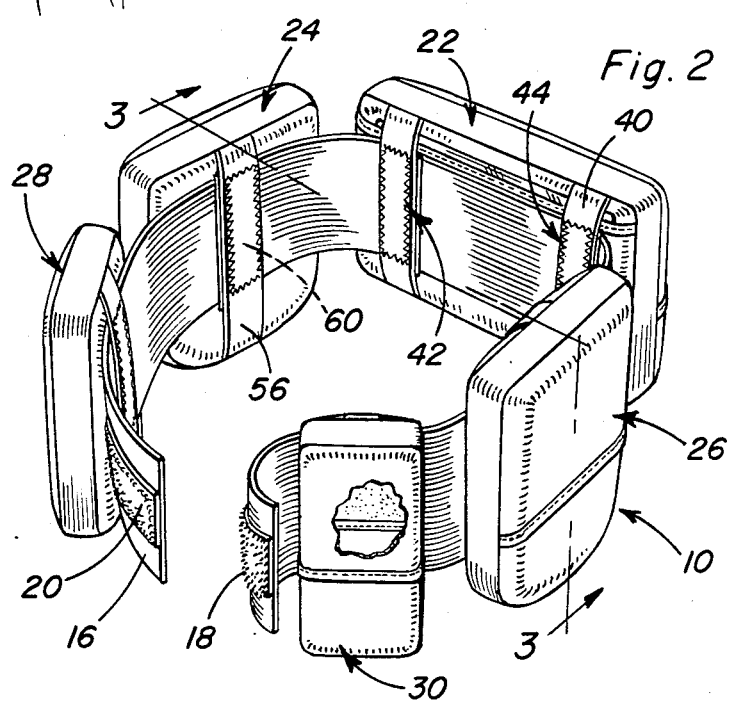
Fig. 2
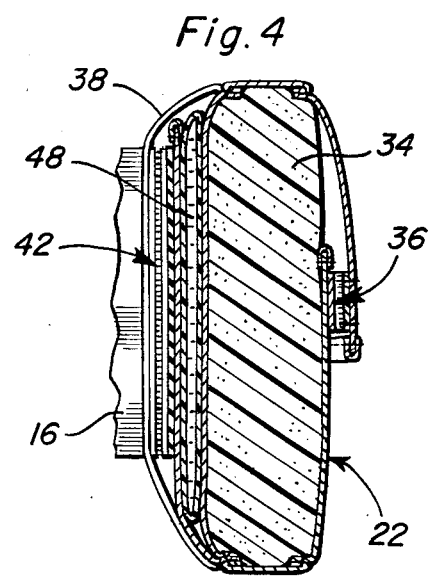
Fig. 4
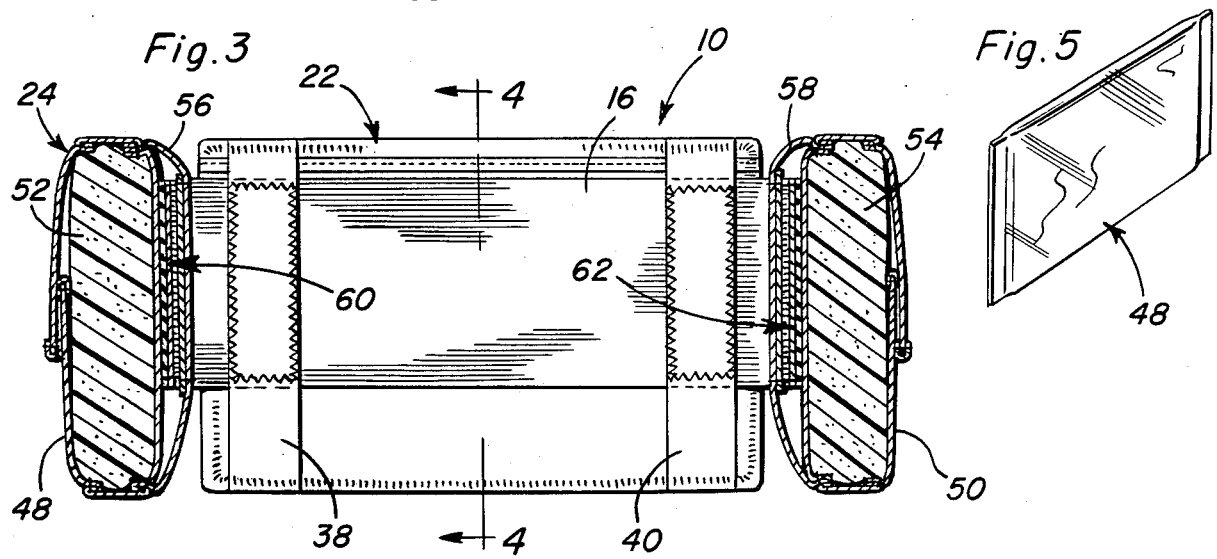
Fig. 3
Fig. 5

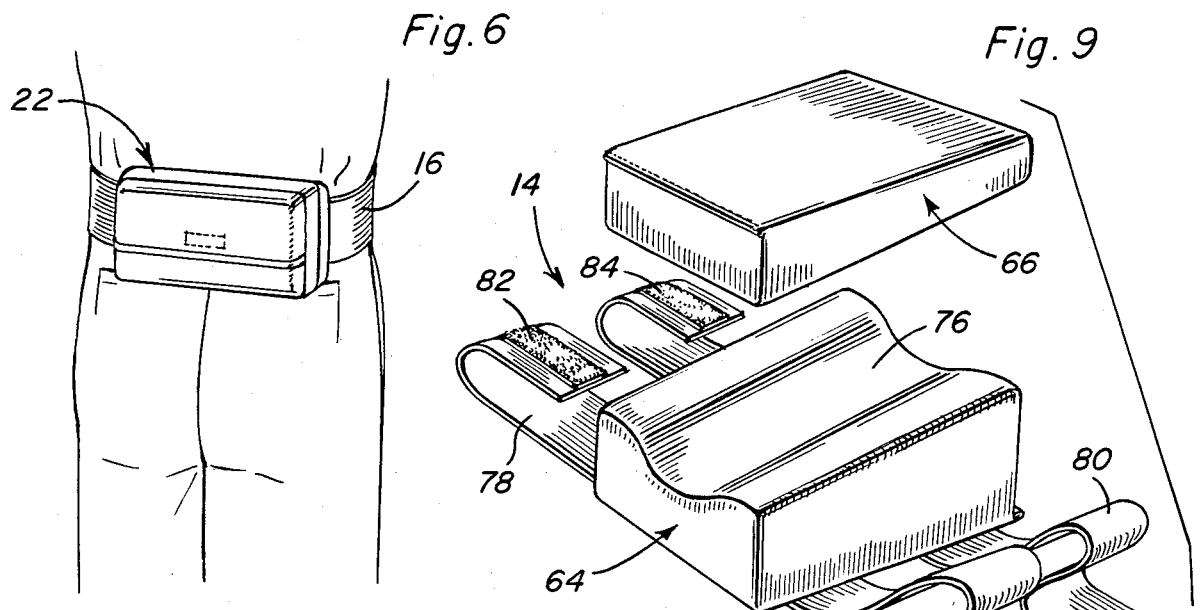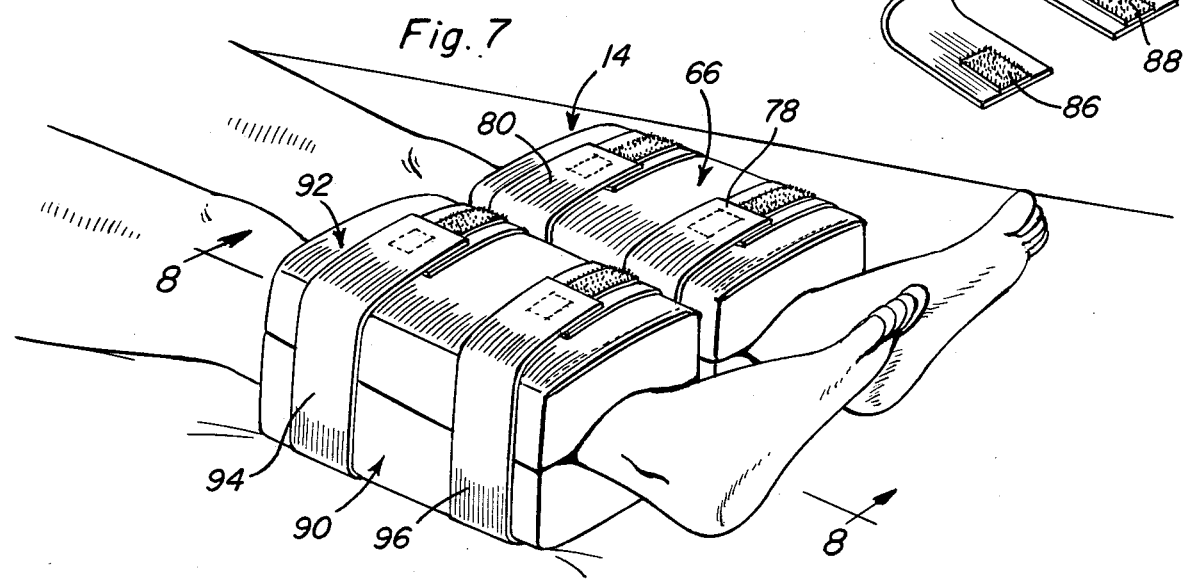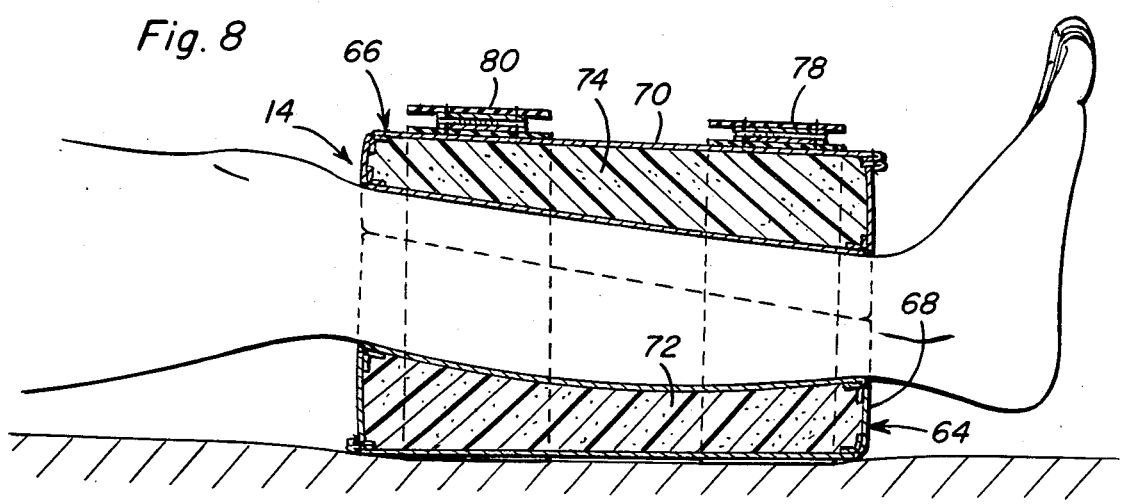

ORTHOPEDIC BELT WITH LEG SUPPORTS

BACKGROUND OF THE INVENTION

This invention relates to apparatus for decreasing stresses and pressure generated to a person's lumbosacral spine while sitting or lying supine, prone or on the side, so as to enable the person sit or to rest with more comfort and minimize aches, pains and stiffness produced by poor sitting or sleeping posture.

For an understanding of the problems with which the present invention is concerned, the anatomy of the lower back and how it relates to posture and the pelvic force couple is of relevance. The pelvic force couple is a dynamic relationship between certain parts of the body and the forces which act upon these parts. The parts of the body making up the spinal column include; vertebrae, i.e. the bony components of the spinal column which permit and limit motion, protect the spinal cord, and support the body in an upright position; discs, i.e. tough, fibrous outer tissues (annulus fibrosis) with soft, jelly-like centers (nucleus pulposus) which act as a cushion between the vertebrae; nerves which communicate feelings and control the muscles; ligaments, i.e. tough, semi-elastic tissues which help to hold the vertebrae together and reinforce the strength of the back; and muscles, i.e. elastic contractable tissues which provide power for motive force and support for the back.

Forces which act upon the back are; the actions of muscles, and the actions of gravity. When these forces operate independently any of the following actions may result. Operation of the back extensor muscles alone may tilt the pelvis forward, increasing the lordotic curve in the lower back. Operation of the quadriceps and hip flexor muscles may also tilt the pelvis forward. Operation of the abdominal muscles may tilt the pelvis backwards decreasing the lordosis in the lower back. Operation of the gluteals and hamstrings may also tilt the pelvis backward, while the force of gravity tends to tilt the pelvis forward. If one or more of the above forces become unbalanced, this may cause problems in the operation of the pelvic force couple. The forces may for example become unbalanced from lack of muscle strength and flexibility, the aging process, wear and tear of degeneration, misuse, such as poor posture and poor body mechanics, or trauma such as torn ligaments, muscle strain, ruptured discs, or damage from disease. With the forces out of balance, a person will be more prone to injury and wear on the back while, if the forces are in balance and the pelvic force couple functions properly, a person will have good muscle support and flexibility, a slight curve in the lower back, and good alignment of the vertebrae and discs with minimal stress and pressure.

The back is affected by every position a person assumes, sitting, stooping, standing, or lying down. When performing daily activities or sitting or sleeping with poor posture a person increases the stress and pressure generated to the lumbosacral spine. This may increase the body's degenerative process, create inflammation, stiffness, pain and/or muscle spasm and disfunction.

The correct anatomical position of the lumbosacral spine is a slight lordosis. Any variation from this position increases the stress and pressure in the lower back. A number of activities during the day, as well as sitting or sleeping postures may cause the lumbosacral area to bow out (extremely flat back) or bow in (extreme lordosis). With proper education and support, the lower back can be maintained in a correct anatomical position. Excessive lordosis is generally due to one or more of the following factors, namely, weak abdominal muscles, overweight, or lazy or incorrect posture. When the lower back is put into excessive lordosis the rear joints in the back are compressed causing an increased wear and tear process and possible inflammation, stiffness and pain/spasm cycle, the hole where the nerve comes out may also narrow, causing pressure and irritation to the nerve root, and a shearing force may be placed on the discs causing the fibers of the discs to wear. When the back is extremely flat (bowed out) the compressive forces may cause a shearing force on a disc, with a similar effect to increased lordosis. Bowing out will stretch the posterior wall of a disc, increase intradiscal pressure and place posterior ligament and muscles in a stretched position.

It is evident from the foregoing that poor posture both during daytime activities, sitting and while lying down or sleeping can have deleterious effects on the back. The present invention is directed toward providing apparatus which can be used while sitting or lying down to provide a person with improved support for the lumbosacral spine reducing stress and promoting proper posture.

DESCRIPTION OF PRIOR ART

The following U.S. patents relate to orthopedic belts, leg supports, and the like. None of these however discloses apparatus having the features of the present invention.

U.S. Pat. Nos. 2,554,337 2,813,526 3,946,451 4,071,031 4,175,548 4,265,232 4,294,239

SUMMARY OF THE INVENTION

The present invention provides apparatus for decreasing stresses and pressures generated to the lumbosacral spine while a person is sitting or lying supine, prone or on the side, the apparatus including, at least in a preferred embodiment thereof, a belt assembly which fits around the waist, and leg supports which attach individually to each leg between the knee and ankle. The sitting belt has one foam pad positioned posteriorly in the lumbosacral area. The sleeping belt assembly has a plurality of foam pads positioned in such a manner to help maintain correct anatomical position of the lumbosacral spine (a slight lordosis) while the person is lying down. The leg supports are designed to help minimize the forces generated in the lumbosacral area from muscular tension and to place the parts of the pelvic force couple into a relaxed position in the prone, supine, or side-lying position.

When sitting or lying supine a person should have proper support beneath the lumbosacral area in order to maintain correct spinal alignment. When lying supine there should also be support behind the legs from the knees to the ankles in order to place the hip flexor muscles in a more relaxed position. When properly supported, all parts of the pelvic force couple will be in a more relaxed state with minimal force in the lumbosacral area. When lying prone, there should be support under the anterior superior iliac spines to prevent the pelvis from rolling forward into an anterior pelvic tilt. While prone, there should also be support under the anterior lower third of the tibia to allow the hamstring muscles to assume a relaxed condition, minimizing muscular forces generated in the lumbosacral spine. When side-lying there should be support between the lateral lower ribs and iliac crest to maintain the spine in its correct anatomical position. A support should also be placed immediately between the knee and ankle to minimize the muscular forces generated by the hip abductors and tensor fascia lata. Apparatus in accordance with the present invention provides for all of the above kinds of support.

The apparatus in accordance with the invention may be made in various sizes to fit persons of different builds, and the sleeping belt pads may comprise a posterior pad, a pair of lateral pads on opposite sides of the posterior pad, and a pair of anterior pads forwardly of the respective lateral pads. The leg supports may, for example, comprise a calf-embracing pad, and a shin-embracing pad which are held around the lower portion of the leg by suitable elasticized straps or the like. The sitting belt may comprise a posterior pad.

The apparatus assists in minimizing stress and pressure in the lower back area while sitting or lying either supine, prone or on the side. The pads on the belt are positioned in such a way as to maintain the proper anatomical position of the lumbosacral spine, namely, a slight lordosis in any and all of the above sitting or lying positions. The leg supports allow the parts of the pelvic force couple to be placed in a more relaxed, less stressful position, and in so doing a person may rest with more comfort and minimize distress and pressure generated to the lumbosacral spine.

These together with other objects and advantages which will become subsequently apparent reside in the details of construction and operation as more fully hereinafter described and claimed, reference being had to the accompanying drawings forming a part hereof, wherein like numerals refer to like parts throughout.

BRIEF DESCRIPTION OF DRAWINGS

FIG. 1 is a side view of a person lying in a supine position and wearing a padded belt in accordance with the invention.

FIG. 2 is a perspective view of a padded belt in accordance with the invention.

FIG. 3 is a sectional view on line 3—3 of FIG. 2, to an enlarged scale.

FIG. 4 is a sectional view on line 4—4 of FIG. 3.

FIG. 5 is a perspective view of a gel pouch which may be used in a belt as shown in FIGS. 2 through 4.

FIG. 6 is a rear view of a person wearing a modified belt in accordance with the invention.

FIG. 7 is a perspective view of a person wearing a pair of leg supports in accordance with the invention.

FIG. 8 is a sectional view on line 8—8 of FIG. 7.

FIG. 9 is an exploded view of a leg support assembly in accordance with the invention.

DESCRIPTION OF PREFERRED EMBODIMENTS

Apparatus in accordance with the invention for decreasing the stress and pressure generated to the lumbosacral spine while a person is sitting or lying down comprises generally a padded belt assembly or lumbar sleeping support 10 shown more particularly in FIGS. 1 through 5, and a pair of leg support assemblies 12 and 14 shown more particularly in FIGS. 7 through 9. While it is preferred, for more beneficial results, to utilize the belt and leg support assemblies in combination, the assemblies may be of benefit in relieving lumbosacral stress and the like when used individually.

Referring in particular to FIGS. 1 through 5, the belt assembly 10 comprises an elasticized orthopedic-type belt 16 of known form for encircling a wearer's waist, the belt having Velcro attachment tabs 18 and 20 at its opposite ends for releasably securing the belt around the wearer's midriff and providing a degree of length adjustment. The belt may, for example, be about 4 inches wide and may be provided in different sizes. Received on the belt are a plurality of support pads including a posterior pad 22, a pair of lateral pads 24, 26 on opposite sides of the posterior pad respectively, and a pair of anterior pads 28, 30 between the lateral pads and the respective ends of the belt.

As shown more particularly in FIG. 4, posterior pad 22 comprises an envelope 32 of suitable fabric in which is located a block or cushion of resilient foam padding material 34. The envelope 32 has adjacent edges with a Velcro fastening 36 defining an opening through which block 34 is inserted. Pad 22 includes a pair of strap loops 38, 40 by means of which the pad is secured on belt 16, and the loops and belt may have interposed Velcro fasteners 42, 44 for securing the pad on the belt in the required position. (In modifications of the invention, the pad may be permanently sewn to the belt, or alternatively, the Velcro fasteners 42, 44 may be omitted so that the position of the pad can be adjusted along the belt.) Pad 22 further includes a portion 46 forming a pocket adjacent straps 38, 40 for a gel pouch 48 shown in FIG. 5. The gel pouch may include a known form of thermal, heat-storage solution which can be used in applying heat to (or in cooling) the adjacent area of the wearer's back.

As shown more particularly in FIG. 3, pads 24 and 26 are of similar construction to pad 22. Thus, pads 24 and 26 comprise fabric envelopes 48, 50 incorporating blocks of resilient cushioning foam 52, 54 in like manner to pad 22. Pads 24 and 26 are secured to belt 16 by single straps 56, 58 and Velcro fasteners 60, 62.

Pads 28 and 30 are of like construction to pads 24 and 26, only the dimensions being varied, and accordingly pads 28 and 30 will not be described herein in detail.

The pads are positioned on belt 16 so as to provide suitable support for the lumbosacral spine when a wearer is sitting or lying supine, prone, or on the side. Thus, as shown in FIG. 1, when the wearer is sitting or lying supine, posterior pad 22 provides support under the lumbosacral area. When lying on the side, one or other of pads 24, 26 provides support under the area between the wearer's lateral lower ribs and the iliac crest. When the wearer is lying prone, anterior pads 28 and 30 provide support under the anterior superior iliac spines.

The sizes, dimensions, and spacing of the various pads may be varied to suit particular individuals, and the apparatus may be manufactured in a range of sizes. For example, the pads may incorporate foam material having a thickness of about 2 inches. For a typical "large" size belt, posterior pad 22 may be about 11 inches long and 6 inches high. Lateral pads 24 and 26 may be about 5 ½ inches wide, with a curved base as illustrated, and about 7 inches high. Anterior pads 28 and 30 may be about 4 inches wide and 8 inches high.

In a modification of the invention designated as a posterior lumbar support, illustrated in FIG. 6, belt 16 may be provided only with a single posterior pad 22 for use for example when a wearer is sitting, or for persons who sleep only on their back. Preferably, for sleeping, the modified form of the invention is also utilized with leg supports shown in FIGS. 6 through 9 and described in more detail below.

Leg support assemblies or leg elevators 12 and 14 are each of similar construction, and accordingly only assembly 14 will be described in detail. With particular reference to FIG. 9, it will be noted that assembly 14 comprises a calf-engaging support pad 64 and a shin-engaging support pad 66. As shown in FIG. 8, pads 64 and 66 comprise fabric envelopes 68, 70 containing respective blocks of foam cushioning material 72, 74 similar to the blocks used in the support pads on belt 16. Pad 64 is of wedge-shaped form and has a longitudinal depression 76 contoured to the calf portion of a person's leg. Pad 66 is of complementary wedge-shaped form. Elasticized straps 78, 80 are sewn to the base of pad 64, the straps having Velcro tabs 82, 84, 86, 88 whereby pads 64 and 66 may be releasably secured together in embracing relation around the lower part of a wearer's leg as shown in FIGS. 7 and 8. As previously noted, pad assembly 12 is of like construction to assembly 14 and comprises a calf-engaging pad 90, a shin-engaging pad 92, and attachment straps 94, 96.

With the leg support assemblies secured around a wearer's legs as shown in FIGS. 7 and 8, when the wearer is lying supine, as illustrated, the leg supports will help in placing the hip flexor muscles in a more relaxed position. When lying prone, the leg support assemblies provide cushioning under the anterior lower third of the tibia to allow the hamstring muscles to be in a more relaxed state, thereby minimizing muscular forces generated in the lumbosacral spine. When lying on the side, the leg support assemblies minimize muscular forces generated by the hip abductors and tensor fascia lata.

It will be appreciated from the foregoing that the invention provides integrated apparatus for relieving stress on the lumbosacral spine when a wearer is sitting or lying down, in order to alleviate back ailments and improve posture in general. The apparatus may be manufactured from readily available materials which may be washed or laundered by conventional techniques. For example, in the belt assembly, the blocks of foam cushioning material may be removed from their respective envelopes, for washing of the belt and envelopes, through the Velcro-fastened openings.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. Apparatus for use in decreasing stresses and pressures to a person's lower back, the apparatus comprising a waist-embracing belt, at least one cushioning pad associated with the belt for strategic positioning between the wearer and a support surface, so as to provide lower back support, and a pair of support pad assemblies for attachment to the wearer's legs between the knee and ankle, for providing support thereto when the wearer is lying supine, prone and on the side, wherein each leg support assembly comprises a first support pad for positioning against the wearer's calf, a second support pad for positioning against the shin, and tie means attaching the pads together around the wearer's leg.

2. The invention of claim 1 wherein the first and second pads are wedge-shaped, and contoured to the lower leg.

3. The invention defined in claim 1 wherein said at least one pad comprises a posterior pad for positioning under the lower back when the person is lying supine or sitting.

4. The invention as defined in claim 3 wherein the posterior pad includes means receiving a thermal pouch for applying heat to, or for cooling, the lower back area.

5. The invention as defined in claim 3 including a pair of lateral support pads associated with the belt on opposite sides of the posterior pad respectively for positioning between the wearer and the support surface in the region of the lower ribs and iliac crest when the wearer is lying on the side.

6. The invention as defined in claim 4 including a pair of anterior support pads associated with the belt on opposite sides of the posterior pad for positioning under the anterior superior iliac spines when the wearer is lying prone.

7. The invention of claim 6 wherein each of said support pads comprises a fabric envelope having a block of resilient foam material received therein and means for attaching said envelope to the belt.

8. The invention of claim 6 wherein the attaching means comprises loop means on each pad and complementary friction fastening means on the belt and the respective loop means for releasably attaching the pads to the belt in required positions.

9. In combination with an orthopedic belt to be worn around the waist of a wearer for providing support to the lower back, a posterior resilient support pad for positioning on the belt under the wearer's lower back area, and further resilient support pads for positioning on the belt on opposite sides of the posterior pad to provide support for areas between the wearer's lateral lower ribs and iliac crest under the anterior superior iliac spines, a pair of leg support assemblies for attachment to the wearer's legs between the knee and ankle for providing support to the legs when the wearer is lying supine, prone and on the side, wherein each leg support assembly comprises a calf-engaging pad, a shin-engaging pad, and tie means for connecting the pads together in embracing relation around the wearer's leg.

10. The invention of claim 9 including a thermal pouch containing a heat storage solution, and means for accommodating said pouch in the posterior pad adjacent the wearer's back.

11. The invention of claim 9 wherein the calf-embracing pad is wedge-shaped and includes a longitudinal depression contoured to fit the calf.

12. An orthopedic leg support assembly for use when a person is lying down to reduce stress on the lumbosacral spine, the assembly comprising a calf-engaging resilient support pad, a shin-engaging resilient support pad, and tie means for securing the pads in embracing relation around the wearer's leg between the knee and ankle, wherein the pads are wedge-shaped and contoured to the leg.

* * * * *